United States Patent [19]

Autenrieth et al.

[11] 4,302,538

[45] Nov. 24, 1981

[54] BUFFER SYSTEM IN AN ANTI-THROMBIN III TEST

[75] Inventors: Stephen M. Autenrieth, Bernardsville; Raymond P. Zolton, Somerville, both of N.J.

[73] Assignee: Ortho Diagnostics Inc., Raritan, N.J.

[21] Appl. No.: 147,810

[22] Filed: May 8, 1980

Related U.S. Application Data

[63] Continuation of Ser. No. 890,734, Mar. 27, 1978, abandoned.

[51] Int. Cl.$^3$ ............................................. C12Q 1/56
[52] U.S. Cl. .................................................. 435/13
[58] Field of Search ....................................... 435/13

[56] References Cited

U.S. PATENT DOCUMENTS

| | | | |
|---|---|---|---|
| 3,884,896 | 5/1975 | Blomback | 435/13 |
| 3,947,378 | 3/1976 | Babson | 435/13 |
| 3,985,618 | 10/1976 | Innerfield | 435/13 |
| 4,106,990 | 8/1978 | Kanges et al. | 435/13 |
| 4,139,415 | 2/1979 | Yin et al. | 435/13 |

OTHER PUBLICATIONS

Abildgaard et al, *Thromb. Diath. Haemorrh.* 24, 224–229 (1970).
Good et al, *Biochemistry*, 5(2), 467–477 (1966).
Innerfield et al, *Amer. J. Clin. Path.*, 65, 64–68 (1976).
Kaulla et al, *Amer. J. Clin. Path.*, 48(1), 69–80 (1967).

*Primary Examiner*—Esther M. Kepplinger
*Attorney, Agent, or Firm*—Goeffrey G. Dellenbaugh

[57] ABSTRACT

Disclosed is a procedure for conducting anti-thrombin III assays in which the conventional thrombin-antithrombin III treatment step is conducted at a pH of 7.9 to 8.5 maintained at the level by a buffer system comprising a buffering amount of N-2-hydroxyethylpiperazine-N'-2-ethanesulfonic acid, N-2-hydroxyethylpiperazine-N'-3-propanesulfonic acid, N-tris-(hydroxymethyl)-methyl-2-amino-ethanesulfonic acid, N-tris-(hydroxymethyl)-methylglycine, or N,N-bis (2-hydroxymethyl)-glycine or a salt thereof. The compositions may also contain bacteriostatic agents.

12 Claims, No Drawings

BUFFER SYSTEM IN AN ANTI-THROMBIN III TEST

This is a continuation, of application Ser. No. 890,734, filed Mar. 27, 1978 now abandoned.

TECHNICAL FIELD

This invention relates to diagnostic tests in in general, and to the diagnostic testing of serum, plasma or other body fluids. More specifically, it relates to a method and composition which will aid in the performance of anti-thrombin III assays irrespective of the previous storage history of the serum or plasma sample being tested.

BACKGROUND

The term "anti-thrombin" was first coined by Morawitz in 1905, and refers to a variety of serum proteins which progressively inactivate thrombin. Hence the term, "anti-thrombin". Anti-thrombin III is one of these anti-thrombins and manifests its effect via interaction with thrombin in circulating blood. This circulating anti-thrombin suppresses the accumulation of thrombin in the circulating system and in that respect acts as an anti-coagulating component. As a result, there is little or no thrombin circulating in the blood of a living host. Were there to be any significant amounts of thrombin, coagulation could begin in vivo and could cause life-threatening episodes.

When a blood sample is taken from a patient, thrombin formation is initiated via conversion of prothrombin in the presence of calcium ions and the thromboplastin produced by the sampling procedure. The thrombin then acts to convert fibrinogen to fibrin to form a clot. To the extent that anti-thrombin III is present, the formation of thrombin and its effects on the conversion of fibrinogen to fibrin is decreased. Therefore, high levels of anti-thrombin III slow down the coagulation procedure. On the other hand, low levels of anti-thrombin III tend to act as pro-coagulants, meaning, of course, that if abnormally short anti-thrombin III assay times are demonstrated by a patient's plasma or serum, that patient may exhibit a predisposition to intra-vascular clotting. While the clinical significance of high levels and low levels of anti-thrombin III varying from the normal ranges has not been fully investigated, there are at least some indications in the literature that low levels are associated with various symptoms of intra-vascular clotting and high levels with symptoms associated with uremic patients and patients on anticoagulant therapy.

PRIOR ART

In 1967, Drs. E. von Kaulla and K. N. von Kaulla published an article in the American Journal of Clinical Pathology, volume 48, pages 69–80, entitled, "Anti-thrombin III and Diseases." In that article, a test system was described which was intended to provide an assay for the determination of the anti-thrombin present in either plasma or serum.

In general, the procedure described is as follows. Thrombin is added to undiluted serum to be analyzed and the mixture allowed to incubate. After a defined period of time, an aliquot of that mixture is withdrawn and added to a pre-warmed solution of fibrinogen. The clotting time of the fibrinogen solution is then noted. That clotting time is a measure of the active thrombin remaining after the incubation of the thrombin and serum mixture, that is, after the anti-thrombin III contained in the serum has partially neutralized the externally added thrombin. Thus, if there had been high levels of anti-thrombin III present in the serum, a low residual thrombin level would result following incubation, leaving low levels of thrombin to react with the fibrinogen, thereby resulting in relatively long times. Therefore, long clotting times from this procedure are indicative of high anti-thrombin III levels in the serum. Conversely, had there been a low level of anti-thrombin III present in the serum, an incomplete reaction with the thrombin would take place leaving a high level of residual thrombin. This high level of thrombin would cause a clot in a short time when added to the fibrinogen solution. Short times in this procedure, therefore, suggest low anti-thrombin III levels in the serum.

Another anti-thrombin III assay was reported in *Thrombosis Diathes. Haemorrh.* 24:224–229 (1970) by U. Abildgaard et al. This procedure, like the von Kaulla procedure, is a two-stage technique for the determination of anti-thrombin III, using preferably plasma as opposed to the preferred serum of the von Kaulla work. In general, however, the Abildgaard and the von Kaulla assays follow generally the same procedure. That is, defibrinated plasma or serum is incubated at about 37° C. with a thrombin source for either three or six minutes. It is during this incubation period that the present invention has relevance, as will be set forth in detail hereafter. In the second stage, an aliquot of the thrombin-plasma (or serum) solution is added to a tube containing a source of fibrinogen and the clotting time of the fibrinogen solution measured as indicated previously.

In the Abildgaard procedure, the pH during the incubation step referred to above is maintained at approximately 8 by utilization of a phosphate buffer at a molarity of 0.053 and an ionic strength of 0.15. The von Kaulla assay does not have any pH control at this point. In still another publication, a buffer comprising tris-(hydroxymethyl) amino methane was used in place of this phosphate buffer. (See Innerfield Amer. J. Clin. Nat'l. 65:64-68, 1976.) In another publication not at all related to the detection of anti-thrombin III, a series of buffers are disclosed some of which are used in the present invention. That literature reference is Good, et al, *Hydrogen Ion Buffers for Biological Research*, Biochemistry pp. 467-477, Volume 5, #2, Feb. 19, 1966.

While there are many specific ways known for conducting an anti-thrombin III assay, virtually all of them include in general the steps of contacting the anti-thrombin III contained in a body fluid, such as serum or plasma, with thrombin, so that the anti-thrombin III partially or wholly neutralizes the thrombin, contacting the residual thrombin with fibrinogen and noting the clotting time of the fibrinogen-treated mixture. The duration of that clotting time, as indicated previously, is a function of the amount of anti-thrombin III originally present in the source. Those skilled in the art will appreciate that assays of the class of which anti-thrombin III is one, are generally performed by preparing standard curves of known concentrations (or base concentrations) plotted against the response elicited by the assay from those base concentrations. Once the curve is established, the assay is performed on a sample containing an unknown concentration of suspect material and the assay results located on the standard curve. The anti-thrombin III concentration on the standard curve corresponding to the assay result on the unknown is then selected as the concentration of the unknown.

By base concentration is meant a source of anti-thrombin III which contains a normal amount of anti-thrombin III (or a known amount) or an amount which can be used as a base or reference. For example, large pools of plasma can be used as a normal frame of reference and even though the amount of anti-thrombin III be unknown, the pool can be designated as "100%" anti-thrombin III activity. The clotting times obtained on the unknown can then be referred to the clotting time obtained on the standard and expressed as a percentage of "normal" anti-thrombin III. When known concentrations are desired for standards and controls these can be independently determined by radioimmunoassay techniques by those skilled in the art.

It is not always possible to utilize collected plasma or serum samples immediately in a test assay. Accordingly, it is quite often necessary either to freeze the samples or to store them at low temperatures (for example 2° to 8° C.). As a result of this, the samples may be subjected to undesirable freeze/thaw cycles. It has been demonstrated in the literature that refrigeration and freeze/thaw cycles have a significant effect on the anti-thrombin III activity displayed by the sample on subsequent measurement. For example, in the Innerfield et al., publication referred to above, the authors report that freezing or refrigeration at 4° C. significantly prolongs the anti-thrombin clotting time. This prolongation is reportedly due to an increase of the pH of the serum during refrigeration. Similarly, Abildgaard reports in the previously mentioned publication on pages 226–227 that the anti-thrombin activity of plasma tends to decrease slowly upon storage, five percent of the activity being lost when the plasma is stored for 48 hours at 37° C., or for about a week at 20° C. or a year at −20° C. Freezing and thawing cycles, however, are reported to cause an additional 10% loss in activity. Although the problems caused by freezing and thawing of samples are to a large extent eliminated by the prior buffer used, the art would be well served by the provision of other readily available buffers.

Accordingly, the present invention provides a buffer system which is compatible with both thimerosal as a preservative, and plasma or serum which have gone through various freeze/thaw cycles. This invention, therefore, manifests itself in a method for conducting an anti-thrombin III assay, and in an additional aspect, in a composition useful for conducting the assay.

DISCLOSURE

In accordance with the present invention, there is now provided an aqueous physiological saline buffer system comprising N-2-hydroxyethyl piperazine-N'-2-ethanesulfonic acid or a salt thereof as a buffering compound, for use in conducting anti-thrombin III assays. The buffering system has a pH which is maintained during the assay in the range of 7.8 to 8.5 and preferably 7.9 to 8.1. Such a system additionally comprising a preservative such as thimerosal has a suitably long shelf life.

As a further aspect, the present invention includes an improvement in the known general method of determining the level of anti-thrombin III in an anti-thrombin III source such as body fluid, serum or plasma for example, by treating the anti-thrombin III source with a known quantity of thrombin thereby to partially neutralize the added thrombin, contacting the residual thrombin with fibrinogen to form a clot, and measuring the time that is required to form the clot, the improvement comprising conducting the thrombin-anti-thrombin treatment step at a pH of between 7.9 to 8.5 maintained by a buffer system comprising a buffering amount of N-hydroxyethylpiperazine-N'-2-ethanesulfonic acid or a salt thereof. It is preferred to use the buffering system of the present invention however, instead of only the sulfonic acid compound (or its salt) described above.

In preparing the buffer system of the present invention, the desired pH may be reached via the addition of a base, such as an alkali metal hydroxide, preferably sodium hydroxide or an acid, preferably a mineral acid such as hydrochloric acid depending on whether the free sulfonic acid or a salt thereof is used. Specifically, the free acid form of the sulfonic acid buffer compound in aqueous solution has a pH of between 5.5 to 6.0. This pH is too low an ambient in which to conduct the anti-thrombin III assay efficiently so that an increase to the desired 7.9 to 8.5 pH level is needed. This may conveniently be achieved by adding an appropriate amount of base. If a salt of the buffer is used, the pH may be too high in which case it is conveniently lowered with a suitable acid such as hydrochloric acid or the like.

A suitable buffer system is prepared from the following amounts of ingredients (weights are per liter of solution).

Buffering compound—(as free acid)—10.0 to 13.5 and preferably 11.5 to 12.5 grams.

Thimerosal—an antibacterially effective amount such as 0.05 to 0.2 and preferably 0.075 to 0.125 grams.

NaCl—sufficient in amount to provide a physiological ionic strength. Values of 1.2 to $1.4 \times 10^{-2}$ mho/cm (at 25° C.) specific conductivity are suitable. This corresponds to approximately 6.5 to 7.0 grams.

Base—sufficient to raise the pH to 7.9 to 8.5. This is conveniently done by adding, for example, a sufficient amount of 1 N NaOH solution, usually of the order of 30–50 ml.

Water—q.s. to one liter.

These compositions are stable for periods of up to 18 months and often longer. Significantly, they do not materially affect the results of the assay and they can be used with either fresh or frozen serum or plasma.

The buffer systems described above are now suitable for use in an anti-thrombin III assay. The actual amount of buffer system used will generally depend upon the ultimate assay employed and the concentration of the buffering compound present in the system.

Using the preferred buffer system described above, an amount of buffer system corresponding to from 3–19 parts per one part of an anti-thrombin III source to be assayed (or in the case of preparation of the standard curve, known amounts of anti-thrombin III) is conveniently used. It should be borne in mind, however, that the actual amount of buffer system used per unit of anti-thrombin III source, is only critical to the extent that it maintains that unit during testing at a pH in the range of 7.9 to 8.5.

The preferred manner of carrying out the test utilizing the buffer of the present invention is as follows:
(1) One part of a source of anti-thrombin III is diluted with four parts of the preferred buffer of the present invention. The anti-thrombin III source may be serum, difibrinated plasma or the like. The dilution is preferred because it tends to dilute the anti-thrombin III activity of the plasma. Thus, while any compatible diluent may be used, it is preferred to use the buffer system since it will be needed in the subsequent thrombin treatment stage.

(2) 0.4 ml of the diluted anti-thrombin III source is pre-warmed to 37° C.

(3) 0.1 ml of a standardized thrombin containing 50±15 NIH units of thrombin per ml is added to the pre-warmed diluted anti-thrombin III source and the resulting mixture incubated for three minutes at 37° C. In steps 1-3, plastic test tubes are employed.

(4) A separate (glass or plastic) test tube containing 0.2 ml of solution of fibrinogen in a second buffer* and containing from 0.7 to 1.0 milligrams of fibrinogen per milliliter is previously pre-warmed at 37° C.

*This buffer solution contains, per liter of solution, 1. Buffering Compound used in the first buffer solution (as the free acid)—7–8.5 and preferably 7.6–8.0 grams. 2. Thimerosal—an antibacterially effective amount such as 0.05 to 0.2 and preferably 0.075 to 0.125 grams. 3. NaCl—Ionic strength of 0.8 to $1.0 \times 10^{-2}$ mho/cm (at 25° C.) specific conductivity. This corresponds to approximately 4.8 to 5.8 grams. 4. Base—sufficient to raise the pH to 6.6 to 7.0. This is conveniently done by using for example sufficient amounts of 1 N NaOH solution of the order of 5 to 15 ml. If a salt of the buffering compound is used, the pH may be too high. In this case, it is conveniently lowered using an appropriate acid, preferably a mineral acid, such as hydrochloric acid or the like. (5) Immediately following the three minute incubation recited for the anti-thrombin III—thrombin mixture, 0.1 ml of that mixture is added to the 0.2 ml fibrinogen solution. (6) With the addition, a timer is started and the time for a clot to form is noted.

The above general procedure can be used to prepare the standard curve and to assay unknowns in accordance with known techniques as described above.

In the above description, the buffer system is described as being used as a diluent for the anti-thrombin III source and thus is carried through the process from the beginning. This however is not critical, it being sufficient that the assay take place in the presence of the buffer commencing with the step mixing the thrombin with the anti-thrombin III source.

While the above description has been given with reference to using thimerosal as the antibacterial compound, it should be apparent that any suitable heavy metal antibacterial compound could be used as well. Indeed, where shelf life is not necessarily desired, but stability against the freeze/thaw cycle previously discussed is more of a problem, the antibacterial compound may be dispensed with entirely. Where one is desired however there may be used mercury salts, such as mercuric acetate, mercuric nitrate, mercuric chloride and the like, and tin salts such as stannous chloride and the like.

Similarly, although the above description has been given with reference to N-hydroxyethylpiperazine-N'-2-ethane sulfonic acid or salts thereof, other buffering compounds or their salts may be employed as well, such as: N-hydroxyethylpiperazine-N'-3-propane sulfonic acid, N-tris-(hydroxymethyl)-methyl-2-aminoethane sulfonic acid, N-tris-(hydroxymethyl)-methyl-glycine and N,N-bis-(2-hydroxymethyl)-glycine. As salts there may be mentioned those obtained by reaction or by addition with such bases and acids respectively as sodium potassium, and ammonium hydroxides and hydrochloric nitric and sulfuric acids. Preferred when salts are used are the reacted salts such as the sodium salt.

The following examples represent specific embodiments of the present invention. In each example, the preferred manner of carrying out the test hereinabove was employed.

EXAMPLE 1

The buffer compound was N-hydroxyethylpiperazine-N'-2-ethane sulfonic acid. The source of anti-thrombin III was a freeze-dried pool of difibrinated human plasma, independently assayed for anti-thrombin III concentration and found to be in the normal range. Three buffer compositions were prepared as follows:

COMPOSITION 190 1

11.9 grams of buffering compound, 0 grams of thimerosal, 6.8 grams of sodium chloride, pH adjusted to 8.0 with 38 ml of 1 N sodium hydroxide solution, Q.S. with water to one liter.

COMPOSITION #2

Identical to the Composition #1 except that it contained 0.005% by weight of thimerosal.

COMPOSITION #3

Identical to #1 except that it contained 0.01% by weight of thimerosal.

Each one of the buffer compositions was utilized in three separate experiments utilizing the preferred manner of carrying out the test described above, each with the same source of anti-thrombin III referred to above. The clotting times on the buffer compositions were as follows:

1. 41.2±0.9 seconds
2. 41.3±0.5 seconds
3. 40.4 seconds

The application of a Student's standard t-test shows that the above numbers are not statistically different from one another. This indicates that thimerosal has no deleterious effect on the performance of the buffer in the anti-thrombin III assay.

Compositions 2 & 3 have been resistant to bacterial contamination for significant periods of time of the order of 18 months or more.

EXAMPLE 2

The purpose of this example was to determine if storage at low temperatures has any effect on anti-thrombin III test results.

Following the general procedure of Example 1, two separate pools of freshly drawn, defibrinated normal pooled plasma were selected and divided into aliquots of 2 ml each. The first aliquot from each pool was subjected to the anti-thrombin III assay described in Example 1 utilizing buffer system #3 from the example and the clotting time arbitrarily assigned the value of 100% anti-thrombin III activity. The normal anti-thrombin III level, against which this was compared, had been independently established by following the procedure of Example 1 utilizing a known anti-thrombin III source.

Each of the other aliquots was frozen and stored at −30° C. At the designated times set forth below, one of the remaining aliquots from each pool was thawed and subjected to the same procedure as the first aliquot. The clotting times were expressed as a percentage of the clotting time obtained on the normal, Day 0 aliquots. The following results were obtained:

TABLE 1

| Days Storage | % AT III (pool 1) | % AT III (pool 2) |
|---|---|---|
| 0 | 100 | 100 |
| 14 | 112 | 103.8 |
| 27 | 102.4 | 108.4 |
| 62 | 107.0 | 103.8 |
| 90 | 101.1 | 96.8 |
| 129 | 103.2 | 104.9 |
| 181 | 97.1 | 100.4 |

The above results have a 4-5% coefficient of variation. This, together with linear regression studies, demonstrates that the clotting times are not significantly different from one another, any actual difference being the result of normal scatter. Hence, the freeze/thaw cycles, at varying stages of storage, had no significant effect on the results of the anti-thrombin III assay.

What is claimed:

1. In the method for determining the anti-thrombin III level of an anti-thrombin III source which includes the steps of treating the source with thrombin whereby the thrombin is wholly or partially neutralized, treating the resulting mixtures with fibrinogen and measuring the clotting time of the fibrinogen treated mixture, the improvement which comprises conducting the thrombin-anti-thrombin III treatment step at a pH of between 7.9 to 8.5 maintained by a buffer system comprising a buffering amount of:
N-2-hydroxyethylpiperazine-N'-2-ethane sulfonic acid, N-2-hydroxyethylpiperazine-N'-3-propane-sulfonic acid, N-tris-(hydroxymethyl)-methyl-2-amino-ethanesulfonic acid, N-tris-(hydroxymethyl)-methyl-glycine, or N,N-bis(2-hydroxymethyl)-glycine or a salt thereof.

2. The method of claim 1 wherein the buffering system has a physiologic ionic strength, and a base or acid sufficient in amount to maintain the pH of the system at 7.9 to 8.5 during said thrombin-anti-thrombin treatment.

3. The method of claim 1 or 2 wherein the buffer system is an aqueous system.

4. The method of claim 3 wherein the anti-thrombin III source is serum or plasma.

5. The method of claim 3 wherein a salt of the buffering compound is used.

6. In the method for determining the anti-thrombin III level of defibrinated serum or plasma which includes the steps of treating the serum or plasma with thrombin whereby the thrombin is wholly or partially neutralized, treating the resulting mixtures with fibrinogen and measuring the clotting time of the fibrinogen treated mixture, the improvement which comprises conducting the thrombin-anti-thrombin III treatment step at a pH of between 7.9 to 8.5 maintained by from three to nineteen parts per part of serum or plasma of an aqueous buffer system having a physiologic ionic strength and comprising a buffering amount of N-2-hydroxyethylpiperazine-N'-2-ethane sulfonic acid or a salt thereof and a base or acid sufficient in amount to maintain the pH of the system at 7.9 to 8.5 during the thrombin-anti-thrombin III treatment step.

7. The method of claim 6 wherein the free sulfonic acid form is used and a base is used to maintain the pH.

8. The method of claim 7 wherein the base is sodium hydroxide.

9. The method of claim 6 wherein the buffering system has sufficient sodium chloride to provide an ionic strength of 1.2 to 1.4 $10^{-2}$ mho/cm at 25° C.

10. The method of claim 6 wherein the buffer system additionally comprises an effective amount of a bacteriostatic agent.

11. The method of claim 7 wherein the aqueous buffer system comprises per liter of buffer solution:
(a) from 100 to 135 grams of N-hydroxyethyl-piperazine-N'-2-ethane sulfonic acid,
(b) 0.05 to 0.2 grams thimerosal and
(c) sufficient NaOH to maintain a pH of 7.9 to 8.5 using said thrombin-anti-thrombin treatment step.

12. In the method for determining the anti-thrombin III level of a defibrinated anti-thrombin III source which includes the steps of treating the source with thrombin whereby the thrombin is wholly or partially neutralized, treating the resulting mixtures with fibrinogen and measuring the clotting time of the fibrinogen treated mixture, the improvement which comprises conducting the thrombin-anti-thrombin III treatment step at a pH of between 7.9 to 8.5 maintained by from three to nineteen parts per part of source of a buffer system comprising a buffering amount of N-2-hydroxyethylpiperazine-N'-2-ethane sulfonic acid or N-tris-(hydroxymethyl)-methyl-2-aminoethane sulfonic acid, or a salt thereof.

* * * * *